United States Patent [19]

Böckmann et al.

[11] Patent Number: 4,764,526
[45] Date of Patent: Aug. 16, 1988

[54] AZOLYLVINYL ETHERS AND PESTICIDAL USE

[75] Inventors: Klaus Böckmann, Cologne; Gerhard Jäger, Leverkusen; Wilhelm Brandes, Leichlingen; Gerd Hänssler; Paul Reinecke, both of Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 27,105

[22] Filed: Mar. 13, 1987

Related U.S. Application Data

[63] Continuation of Ser. No. 727,962, Apr. 26, 1985, abandoned.

[30] Foreign Application Priority Data

May 11, 1984 [DE] Fed. Rep. of Germany ....... 3417468

[51] Int. Cl.$^4$ .................. A01N 43/50; A01N 43/653; C07D 233/58; C07D 241/12
[52] U.S. Cl. .................................. 514/383; 514/184; 514/399; 548/101; 548/262; 548/341
[58] Field of Search ............... 548/101, 262, 341; 514/184, 383, 399

[56] References Cited

U.S. PATENT DOCUMENTS

| | | | |
|---|---|---|---|
| 4,210,657 | 7/1980 | Zirngibl et al. | 548/341 X |
| 4,291,044 | 9/1981 | Jäger et al. | 548/262 X |

FOREIGN PATENT DOCUMENTS

| | | |
|---|---|---|
| 0079856 | 5/1983 | European Pat. Off. |
| 149235 | 12/1984 | European Pat. Off. |
| 170831 | 6/1985 | European Pat. Off. |
| 2610022 | 9/1976 | Fed. Rep. of Germany |
| 2638470 | 3/1977 | Fed. Rep. of Germany |
| 2757113 | 6/1979 | Fed. Rep. of Germany |
| 2839388 | 3/1980 | Fed. Rep. of Germany |
| 3313499 | 10/1984 | Fed. Rep. of Germany |
| 02552 | 8/1982 | PCT Int'l Appl. |

OTHER PUBLICATIONS

Research Disclosure, Industrial Opportunities Ltd., Hampshire, England (Jun. 1982) Abstract 21844.

Primary Examiner—Richard L. Raymond
Attorney, Agent, or Firm—Sprung Horn Kramer & Woods

[57] ABSTRACT

Pesticidally active novel azolylvinyl ethers of the formula

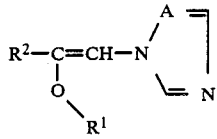

in which

A represents a nitrogen atom or the CH group, $R^1$ represents alkyl, alkenyl, alkinyl, alkoxyalkyl, optionally substituted phenyl, optionally substituted phenylalkyl, optionally substituted phenoxyalkyl, optionally substituted phenoxyalkoxyalkyl, naphthoxyalkyl, optionally substituted cycloalkyl or optionally substituted cycloalkylalkyl, $R^2$ represents alkyl, halogenoalkyl, optionally substituted cycloalkyl or the grouping $R^3$—$C(CH_3)_2$—, or also represents optionally substituted phenyl, if $R^1$ represents optionally substituted phenoxyalkyl or optionally substituted phenoxyalkoxyalkyl and A represents a nitrogen atom, and $R^3$ represents in each case optionally substituted phenyl, phenoxy or phenoxyalkyl, or addition products thereof with acids or metal salts.

9 Claims, No Drawings

AZOLYLVINYL ETHERS AND PESTICIDAL USE

This is a continuation of application Ser. No. 727,962, filed Apr. 26, 1985 and now abandoned.

The present invention relates to new azolylvinyl ethers, a process for their preparation and their use as fungicides and as ectoparasiticidal agents.

It is already known that certain 1-ethene-azolyl derivatives, such as, for example, 2-(4-chlorophenoxy)-4,4-dimethyl-1-(imidazol-1-yl)- and (1,2,4-triazol-1-yl)-1-penten-3-one, have good fungicidal properties (compare DE-OS (German Published Specification) No. 2,846,980).

It is also already known that certain arylvinylazolyl ethers have good fungicidal properties (compare DE-OS (German Published Specification) No. 2,757,113, DE-OS (German Published Specification) No. 2,839,388 and EP-OS (European Published Specification) No. 0,079,856).

It is furthermore already known that disulphides, such as, for example, zinc ethylene-1,2-bisdithiocarbamidate, are good agents for combating fungal plant diseases (compare R. Wegler, "Chemie der Pflanzenschutz- und Schadlingsbekampfungsmittel" ("Chemistry of plant protection agents and agents for combating pests"), Volume 2, page 59 et seq., Springer Verlag 1970).

However, the action of these compounds is not always completely satisfactory in certain fields of indication, especially when low amounts and concentrations are applied.

New azolylvinyl ethers of the general formula (I)

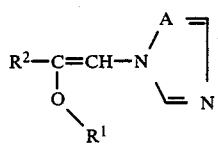
(I)

in which
A represents a nitrogen atom or the CH group,
R$^1$ represents alkyl, alkenyl, alkinyl, alkoxyalkyl, optionally substituted phenyl, optionally substituted phenylalkyl, optionally substituted phenoxyalkyl, optionally substituted phenoxyalkoxyalkyl, naphthoxyalkyl, optionally substituted cycloalkyl or optionally substituted cycloalkylalkyl,
R$^2$ represents alkyl, halogenoalkyl, optionally substituted cycloalkyl or the grouping R$_3$—C(CH$_3$)$_2$—, or also represents optionally substituted phenyl, if R$^1$ represents optionally substituted phenoxyalkyl or optionally substituted phenoxyalkoxyalkyl and A represents a nitrogen atom, and
R$^3$ represents in each case optionally substituted phenyl, phenoxy or phenoxyalkyl,
and acid addition salts and metal salt complexes thereof have been found.

The compounds of the formula (I) can exist in two geometric isomer forms, depending on the arrangement of the groups bonded to the double bond; they are preferentially obtained in a varying isomer ratio. The present invention relates both to the individual isomers and to the isomer mixtures.

It has furthermore been found that the new azolylvinyl ethers of the formula (I) are obtained by a process in which azolylmethyl ketones of the formula (II)

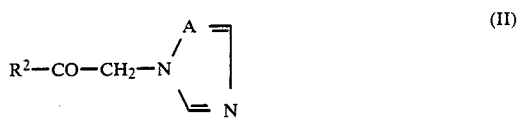
(II)

in which
A and R$^2$ have the abovementioned meaning, are reacted with compounds of the formula (III)

(III)

in which
R$^1$ has the abovementioned meaning and
Z represents an electron-attracting leaving grouping, in the presence of a strong base and in the presence of an aprotic, polar diluent, or in an aqueous-organic two-phase system in the presence of a phase transfer catalyst.

If appropriate, an acid or a metal salt can then be added on to the compounds of the formula (I) thus obtained.

It has furthermore been found that the new azolylvinyl ethers of the formula (I) have powerful fungicidal properties and are also suitable for combating ectoparasites in the field of animal husbandry and animal breeding.

Surprisingly, the compounds according to the invention exhibit better funigicidal actions than the compounds 2-(4-chlorophenoxy)-4,4-dimethyl-1-(imidazol-1-yl)- and (1,2,4-triazol-1-yl)-1-penten-3-one and zinc ethylene 1,2-bisdithiocarbamidate, which are known from the prior art. The active compounds according to the invention thus represent an enrichment of the art.

Formula (I) provides a general definition of the azolylvinyl ethers according to the invention. In this formula, preferably, A represents a nitrogen atom or the CH group;
R$^1$ represents straight-chain or branched alkyl with 1 to 12 carbon atoms, alkenyl or alkinyl with in each case 2 to 20 carbon atoms, alkoxyalkyl with 1 to 4 carbon atoms in each alkyl part or naphthoxyalkyl with 1 to 4 carbon atoms in the alkyl part, or represents phenyl, phenylalkyl with 1 to 4 carbon atoms in the alkyl part, phenoxyalkyl with 1 to 4 carbon atoms in the alkyl part and phenoxyalkoxyalkyl with 1 to 4 carbon atoms in each alkyl part, each of which is optionally monosubstituted or polysubstituted by identical or different substituents in the phenyl part, substituents on the phenyl which may be mentioned in each case being: halogen, alkyl and alkoxy with in each case 1 to 4 carbon atoms, halogenoalkyl, halogenoalkoxy and halogenoalkylthio with in each case 1 or 2 carbon atoms and 1 to 5 identical or different halogen atoms, nitro, cyano, in each case optionally halogen-substituted phenyl, phenoxy and phenylalkyl with 1 to 4 carbon atoms in the alkyl part, and cycloalkyl which has 5 to 7 carbon atoms and is optionally substituted by alkyl with 1 to 4 carbon atoms; or
R$^1$ furthermore preferably represents cycloalkyl or cycloalkylalkyl with in each case 5 to 7 carbon atoms in the cycloalkyl part and 1 to 4 carbon atoms in the alkyl part and in each case optionally monosubstituted or polysubstituted by identical or different alkyl radicals with 1 to 4 carbon atoms;
R$^2$ represents straight-chain or branched alkyl with 1 to 8 carbon atoms, halogeno-tert,-butyl with 1 or 2 halogen atoms or the grouping $R^3$—C(CH$_3$)$_2$—, or represents cycloalkyl which has 5 to 7 carbon atoms and is optionally monosubstituted or polysubstituted by identical or different alkyl radicals with 1 to 4 carbon atoms; or furthermore also represents phenyl which is optionally monosubstituted or polysubstituted by identical or different substituents, possible substituents being the substituents on phenyl already mentioned for $R^1$, if $R^1$ represents optionally substituted phenoxyalkyl or optionally substituted phenoxyalkoxyalkyl and A represents a nitrogen atom; and $R^3$ represents phenyl, phenoxy or phenoxyalkyl with 1 to 4 carbon atoms in the alkyl part, in each case optionally monosubstituted or polysubstituted by identical or different substituents in the phenyl part.

Particularly preferred compounds of the formula (I) are those in which

A represents a nitrogen atom or the CH group;

$R^1$ represents straight-chain or branched alkyl with 1 to 8 carbon atoms, or represents alkenyl with 2 to 18 carbon atoms or alkinyl with 2 to 6 carbon atoms, or represents alkoxyalkyl with 1 to 4 carbon atoms in the alkoxy part and 1 or 2 carbon atoms in the alkyl part, or represents naphthoxyalkyl with 1 or 2 carbon atoms in the alkyl part; or, furthermore, represents phenyl, phenylalkyl with 1 or 2 carbon atoms in the alkyl part, phenoxyalkyl with 1 or 2 carbon atoms in the alkyl part or phenoxyalkoxyalkyl with 1 or 2 carbon atoms in each alkyl part, in each case optionally mono-, di- or tri-substituted by identical or different substituents in the phenyl part, substituents on the phenyl which may be mentioned in each case being: fluorine, chlorine, bromine, straight-chain or branched alkyl with 1 to 4 carbon atoms, methoxy, trifluoromethyl, trifluoromethoxy, trifluoromethylthio, nitro and cyano, phenyl, phenoxy and phenylalkyl with 1 to 3 carbon atoms in the alkyl part, in each case optionally substituted by chlorine or fluorine, cyclopentyl and cyclohexyl; or represents cyclopentyl, cyclohexyl, cyclopentylmethyl, cyclohexylmethyl, cyclopentylethyl or cyclohexylethyl, in each case optionally mono- or di-substituted by identical or different substituents from the group comprising methyl, ethyl and isopropyl;

$R^2$ represents straight-chain or branched alkyl with 1 to 6 carbon atoms, or represents fluorotert.-butyl, chloro-tert.-butyl, 1,1-bis-(fluoromethyl)-ethyl, 1,1-bis-(chloromethyl)-ethyl or the grouping $R^3$—C(CH$_3$)$_2$—, or represents cyclopentyl or cyclohexyl, in each case optionally mono- or di-substituted by identical or different substituents from the group comprising methyl, ethyl and isopropyl; or furthermore also represents phenyl which is optionally mono-, di- or tri-substituted by identical or different substituents, possible substituents being the substituents on phenyl already mentioned for $R^1$, if $R^1$ represents optionally substituted phenoxyalkyl or optionally substituted phenoxyalkoxyalkyl and A represents a nitrogen atom; and $R^3$ represents phenyl, phenoxy or phenoxyalkyl with 1 or 2 carbon atoms in the alkyl part, in each case optionally mono-, di- or tri-substituted by identical or different substituents in the phenyl part, possible substituents being the substituents on phenyl already mentioned for $R^1$.

Preferred compounds according to the invention are also the addition products of acids and those azolylvinyl ethers of the formula (I) in which the substituents A, $R^1$ and $R^2$ have the meanings which have already been mentioned as preferred for these substituents.

Preferred acids which can be added on include hydrogen halide acids, such as, for example, hydrochloric acid and hydrobromic acid, in particular hydrochloric acid, and furthermore phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as p-toluenesulphonic acid and 1,5-naphthalenedisulphonic acid.

Compounds according to the invention which are also preferred are addition products of salts of metals of main groups II to IV and of sub-groups I and II and IV to VIII and those azolylvinyl ethers of the formula (I) in which the substituents A, $R^1$ and $R^2$ have the meanings which have already been mentioned as preferred for these substituents.

Salts of copper, zinc, manganese, magnesium, tin, iron and nickel are particularly preferred here. Possible anions of these salts are those which are derived from those acids which lead to physiologically acceptable addition products. In this connection, particularly preferred acids of this type are the hydrogen halide acids, such as, for example, hydrochloric acid and hydrobromic acid, and nitric acid and sulphuric acid.

If, for example, 3,3-dimethyl-1-(1,2,4-triazol-1-yl)-2-butanone and 4-chlorophenoxyethyl p-toluenesulphonate in the presence of sodium hydride are used as starting substances, the course of the reaction in the process according to the invention can be represented by the following equation:

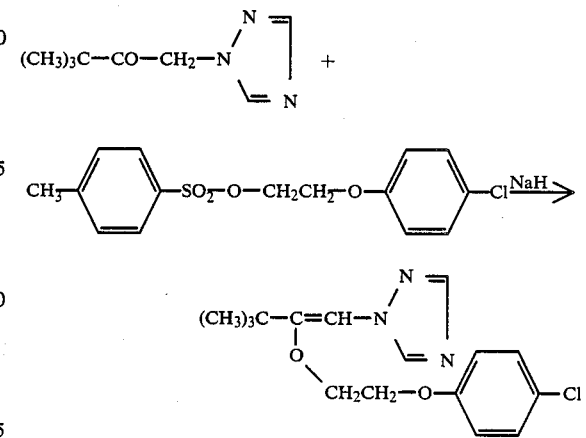

Formula (II) provides a general definition of the azolylmethyl ketones to be used as starting substances in carrying out the process according to the invention. In this formula, A and $R^2$ preferably represent the radicals which have already been mentioned as preferred for these substituents in connection with the description of the substances of the formula (I) according to the invention.

The azolylmethyl ketones of the formula (II) are known (in this context, compare, for example, DE-OS (German Published Specification) No. 2,431,407, DE-OS (German Published Specification) No.

2,610,022, DE-OS (German Published Specification) No. 2,638,470, U.S. application Ser. No. 438,086, filed Nov. 1, 1982, now pending, and U.S. Pat. No. 4,492,795) and are obtained in a generally known manner by reacting corresponding halogenomethyl ketones with imidazole or 1,2,4-triazole in the presence of a diluent, such as, for example, acetonitrile and in the presence of an acid-binding agent, such as, for example, potassium carbonate.

Formula (III) provides a general definition of the compounds also to be used as starting substances for the process according to the invention. In this formula, $R^1$ preferably represents those radicals which have already been mentioned as preferred for this substituent in connection with the description of the substances of the formula (I) according to the invention. Z preferably represents an electron-attracting leaving grouping, such as, for example, halogen, p-methylphenylsulphonyloxy, the grouping —O—$SO_2$—OR or —$NR_3$— and the like, R here representing, for example, alkyl with 1 to 4 carbon atoms.

The compounds of the formula (III) are generally known compounds of organic chemistry.

Possible diluents for the process according to the invention are aprotic, polar solvents. These include, preferably, dimethylformamide, dimethylacetamide, dimethylsulphoxide, N-methylpyrrolidine, 2-pyrrolidinone and hexamethylphosphoric acid triamide. In some cases, it may be advantageous to mix these solvents with other customary inert organic solvents, such as, for example, aromatic hydrocarbons.

The process according to the invention is carried out in the presence of a strong base. All the usual organic and, in particular, inorganic bases can be employed here, such as, preferably, alkali metal hydrides, hydroxides or carbonates, for example sodium hydride and sodium hydroxide; and tertiary amines, such as triethylamine, piperidine and pyridine.

The reaction temperatures can be varied within a substantial range in carrying out the process according to the invention. In general, the reaction is carried out between 0° C. and 120° C., preferably between 20° C. and 100° C.

In carrying out the process according to the invention, 1 to 2 moles of the compound of the formula (III) are preferably employed per mole of azolylmethyl ketone of the formula (II). The end products of the formula (I) are isolated in the generally customary manner. Any by-products formed by alkylation on the $CH_2$ group which may arise are thereby also removed in the customary manner, for example by column chromatography, distillation or recrystallization.

The process according to the invention can also be carried out in a two-phase system, such as, for example, aqueous sodium hydroxide solution or potassium hydroxide solution, toluene or methylene chloride, if appropriate with the addition of 0.1 to 1 mole of a phase transfer catalyst, such as, for example, ammonium or phosphonium compounds, examples which may be mentioned being benzyldodecyl-dimethylammonium chloride and triethyl-benzyl-ammonium chloride.

The acid addition salts of the compounds of the formula (I) can be obtained in a simple manner by customary salt formation methods, for example by dissolving the compound of the formula (I) in a suitable inert solvent and adding the acid, e.g. hydrochloric acid, and can be purified, if appropriate, by washing with an organic solvent.

The metal salt complexes of compounds of the formula (I) can be obtained in a simple manner by customary processes, thus, for example, by dissolving the metal salt in alcohol, for example ethanol, and adding the solution to compounds of the formula (I). The metal salt complexes can be purified in a known manner, for example by filtration.

The active compounds according to the invention exhibit a powerful microbicidal action and can be employed in practice for combating undesired micro-oranisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Venturia species, such as against the apple scab causative organism (*Venturia inaequalis*); rice diseases, such as *Pyricularia oryzae* and *Pellicularia sasakii;* and cereal diseases, such as cereal mildew, *Cochliobolus sativus, Drechslera graminea, Leptosphaeria nodorum* and *Pyrenophora teres.*

Some causative organisms of fungal and bacterial diseases which fall under the generic names listed above may be mentioned as examples, but not by way of limitation: Botrytis species, such as, for example, *Botrytis cinerea;* Plasmopara species, such as, for example, *Plasmopara viticola;* Uromyces species, such as, for example, *Uromyces appendiculatus;* Sphaerotheca species, such as, for example, *Sphaerotheca fuliginea;* Venturia species, such as, for example, *Venturia inaequalis;* Podosphaera species, such as, for example, *Podosphaera leucotricha;* Phytophthora species, such as, for example, *Phytophthora infestans;* Erysiphe species, such as, for example, *Erysiphe graminis;* Puccinia species, such as, for example, *Puccinia recondita;* Fusarium species, such as, for example, *Fusarium culmorum;* Ustilago species, such as, for example, *Ustilago nuda* or *Ustilago avenae;* Septoria species, such as, for example, *Septoria nodorum;* Tilletia species, such as, for example, *Tilletia caries;* Xanthomonas species, such as, for example, *Xanthomonas oryzae;* Pseudomonas species, such as, for example, *Pseudomonas lachrymans;* Pyricularia species, such as, for example, *Pyricularia oryzae,* Pellicularia species, such as, for example, *Pellicularia sasakii;* Pyrenophora species, such as for example, *Pyrenophora teres* (conidia form Drechslera, Syn. Helminthosporium); Cochliobolus species, such as, for example, *Cochliobolus sativus* (conidia form Drechslera, Syn. Helminthosporium), Cercosporia species, such as, for example, *Cercospora canescens.*

It should be emphasized that the substances according to the invention not only have a protective action but in some cases are also systemic. Thus, it is possible to protect plants from fungal attack if the active compounds are fed to the above-ground parts of the plant via the soil and the root or via the seed.

When used in appropriate amounts, the substances according to the invention also exhibit growth-regulating properties.

The active compounds according to the invention are also suitable for combating ectoparasites in the field of animal husbandry and animal breeding, it being possible to achieve better results by combating the pets, for example higher milk outputs, heavier weight, more attractive animal coat, longer life and the like.

In these fields, the active compounds according to the invention are used in the known manner, such as by external application in the form, for example, of dipping, spraying, pouring on and spotting on and dusting, or by oral administration, for example via the feed or drinking water, in the form of, for example, tablets, capsules, drinks and granules.

The active compounds can be converted to the customary formulations, such as solutions, emulsions, wettable powders, suspensions, powders, dusts, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strong polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for examle ligninsulphite waste liquors and methylcellulose.

Adhesive such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs and azo-metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulation or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

When used as ectoparasiticidal agents, the active compound content of the use forms prepared from the commercially available formulations can be varied within wide limits. The active compound concentration of the use forms can be from 0.0000001 to 95% by weight of active compound, preferably between 0.0001 and 1% by weight.

PREPARATION EXAMPLES

Example 1

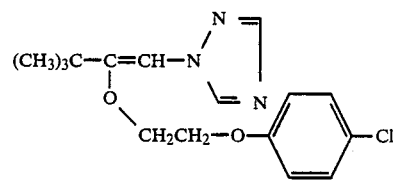

A solution of 1678 (1 mol) 3,3-dimethyl-1-(1,2,4-triazol-1-yl)-2-butanone in 400 ml of dry dimethylformamide is added dropwise to a mixture of 30 g of sodium hydride (80% strength) and 100 ml of dry dimethylformamide at room temperature. The mixture is stirred at 35° C. until the solution is clear, and a solution of 330 g of 2-(4-chlorophenoxy)-ethyl 4-methylphenylsulphonate in 500 ml of dry dimethylformamide is then added dropwise at room temperature. The reaction mixture is stirred at 40° C. for 12 hours and poured onto 3 liters of water. It is extracted three times with 750 ml of ethyl acetate each time and the combined organic phases are washed three times with 500 ml of water each time, dried over sodium sulphate and concentrated in vacuo. The residue is distilled.

253 g (78.8% of theory) of 3,3-dimethyl-2-(4-chlorophenoxyethoxy)-1-(1,2,4-triazol-1-yl)-1-butene of boiling point 185° C./0.1 mbar are obtained.

The followng compounds of the formula (I) can be obtained in a corresponding manner in accordance with the process conditions described:

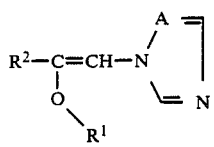

(I)

| Example No. | R¹ | R² | A | Melting point (°C.) or boiling point (°C.)/mba or $n_D^{20}$ |
|---|---|---|---|---|
| 2 | —CH₂CH₂—O—C₆H₅ | $(CH_3)_3C-$ | N | 1.5140 |
| 3 | —CH₂CH₂—O—(2,4-Cl₂C₆H₃) | $(CH_3)_3C-$ | N | 62–66 |
| 4 | —CH₂CH₂—O—(2-ClC₆H₄) | $(CH_3)_3C-$ | N | 51 |
| 5 | —CH₂CH₂—O—(4-C(CH₃)₃C₆H₄) | $(CH_3)_3C-$ | N | 57–58 |
| 6 | —CH₂CH₂—O—(4-C₆H₅C₆H₄) | $(CH_3)_3C-$ | N | 86–100 |
| 7 | —CH₂CH₂—O—(4-FC₆H₄) | $(CH_3)_3C-$ | N | 1.5215 |
| 8 | —CH₂CH₂—O—CH₂CH₂—O—(4-ClC₆H₄) | $(CH_3)_3C-$ | N | 250/0.1 |
| 9 | —CH₂CH₂—O—(4-NO₂C₆H₄) | $(CH_3)_3C-$ | N | 98 |
| 10 | —C₄H₉—n | $(CH_3)_3C-$ | N | 100–105/0.2 |
| 11 | —CH₂CH₂—O—C₂H₅ | $(CH_3)_3C-$ | N | 117–121/0,3 |
| 12 | —CH₂—C₆H₁₁ | $(CH_3)_3C-$ | N | 53 |

-continued

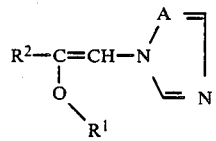
(I)

| Example No. | R¹ | R² | A | Melting point (°C.) or boiling point (°C.)/mba or $n_D^{20}$ |
|---|---|---|---|---|
| 13 | −CH₂CH₂−O−(2,4,6-trichlorophenyl) | (CH₃)₃C− | N | 42 |
| 14 | −CH₂CH₂−O−(4-chlorophenyl) | 4-chlorophenyl | N | 115 |
| 15 | −CH₂CH₂−O−(2-chlorophenyl) | 4-chlorophenyl | N | 134 |
| 16 | −CH₂CH₂−O−phenyl | 4-chlorophenyl | N | 64–66 |
| 17 | −CH₂CH₂−O−(4-tert-butylphenyl) | 4-chlorophenyl | N | 96 |
| 18 | −CH₂CH₂−O−(2,4-dichlorophenyl) | 2,4-dichlorophenyl | N | 104 |
| 19 | −CH₂CH₂−O−phenyl | 2,4-dichlorophenyl | N | 63–64 |
| 20 | −CH₂CH₂−O−(4-fluorophenyl) | 2,4-dichlorophenyl | N | 85–89 |
| 21 | −CH₂CH₂−O−(4-chlorophenyl) | 2,4-dichlorophenyl | N | 145 |
| 22 | −CH₂CH₂−O−(4-chlorophenyl) | 1-methylcyclohexyl (H) | N | 1.5520 |

-continued

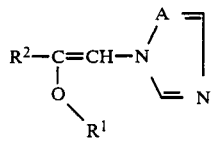
(I)

| Example No. | R¹ | R² | A | Melting point (°C.) or boiling point (°C.)/mba or $n_D^{20}$ |
|---|---|---|---|---|
| 23 | —CH₂CH₂—O—(2,4-Cl₂-C₆H₃) | (CH₃)₃C— | CH | 62–66 |
| 24 | —CH₂CH₂—O—(4-Cl-C₆H₄) | (CH₃)₃C— | CH | 49–52 |
| 25 | —CH₂CH₂—O—(2-Cl-C₆H₄) | (CH₃)₃C— | CH | 65–70 |
| 26 | —CH₂CH₂—O—(4-F-C₆H₄) | (CH₃)₃C— | CH | 83–85 |
| 27 | —CH₂CH₂—O—(4-C₆H₅-C₆H₄) | (CH₃)₃C— | CH | 117–119(Form A)* |
| 28 | —CH₂CH₂—O—(4-CH₃-C₆H₄) | (CH₃)₃C— | CH | 103–105 |
| 29 | —CH₂CH₂—O—(4-C(CH₃)₃-C₆H₄) | (CH₃)₃C— | CH | 53–60 |
| 30 | —CH₂CH₂—O—(4-NO₂-C₆H₄) | (CH₃)₃C— | CH | 46 |
| 31 | —CH₃ | (CH₃)₃C— | CH | 95/0.2 |
| 32 | —C₄H₉—n | (CH₃)₃C— | CH | 100/0.2 |
| 33 | —CH₂CH₂—O—C₂H₅ | (CH₃)₃C— | CH | 112–115/0.3 |
| 34 | —CH₂—CH(C₂H₅)₂ | (CH₃)₃C— | CH | 115–118/0.3 |
| 35 | —CH₂—CH(C₂H₅)—C₃H₇—n | (CH₃)₃C— | CH | 124–129/0.3 |
| 36 | —CH₂(CH₂)₇CH=CH(CH₂)₇CH₃ | (CH₃)₃C— | CH | 1,4828(Form A)* |
| 37 | —CH₂(CH₂)₇CH=CH(CH₂)₇CH₃ | (CH₃)₃C— | CH | 1,4819 |
| 38 | —CH₂—(cyclohexyl) | (CH₃)₃C— | CH | 128–135/0.3 |

-continued

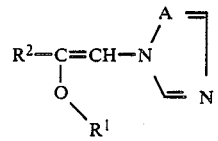

(I)

| Example No. | R¹ | R² | A | Melting point (°C.) or boiling point (°C.)/mba or $n_D^{20}$ |
|---|---|---|---|---|
| 39 | −CH₂CH₂−O−(2,4,6-trichlorophenyl) | $(CH_3)_3C-$ | CH | 62 |
| 40 | −CH₂CH₂−O−(4-methylphenyl) | $(CH_3)_3C-$ | CH | 70 |
| 41 | −CH₂CH₂−O−(4-cyclohexylphenyl) | $(CH_3)_3C-$ | CH | 78 |
| 42 | −CH₂CH₂−O−(2-methyl-4-chlorophenyl) | $(CH_3)_3C-$ | CH | 55 |
| 43 | −CH₂CH₂−O−(4-cumylphenyl) [4-(2-phenylpropan-2-yl)phenyl] | $(CH_3)_3C-$ | CH | 1.5631 |
| 44 | −CH₂CH₂−O−(2,6-dimethylphenyl) | $(CH_3)_3C-$ | CH | 160/0.2 |
| 45 | −CH₂CH₂−O−(1-naphthyl) | $(CH_3)_3C-$ | CH | 204/0.1 |
| 46 | −CH₂CH₂−O−(2-naphthyl) | $(CH_3)_3C-$ | CH | 103 |
| 47 | −CH₂CH₂−O−(4-chlorophenyl) | $(CH_3)_2CH-C(CH_3)_2-$ | CH | 190/0.1 |
| 48 | −CH₂CH₂−O−(4-chlorophenyl) | $FCH_2-C(CH_3)_2-$ | CH | 194/0.1 |

-continued $$R^2-\underset{\underset{R^1}{\overset{|}{O}}}{C}=CH-N\overset{A\,=}{\underset{=\!N}{\diagdown}}\qquad (I)$$

| Example No. | R¹ | R² | A | Melting point (°C.) or boiling point (°C.)/mba or $n_D^{20}$ |
|---|---|---|---|---|
| 49 | —CH₂CH₂—O—⟨C₆H₄⟩—Cl | cyclohexyl with CH₃, H | CH | 1.5310 |
| 50 | —CH₂CH₂—O—⟨C₆H₄⟩—C(CH₃)₃ | cyclohexyl with CH₃, H | N | 1.5538 |
| 51 | —C₄H₉—n | 2,4-Cl₂-C₆H₃-O-CH₂-C(CH₃)₂— | CH | 1.5392 |
| 52 | —CH₂CH₂—O—⟨C₆H₄⟩—C(CH₃)₃ | cyclohexyl with CH₃, H | CH | 1.5395 |

*Form A = one of the two possible geometric isomer forms

USE EXAMPLES

The compounds shown below are used as comparison substances in the following examples:

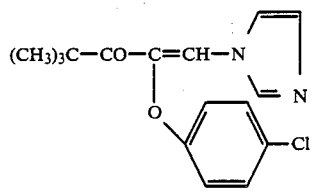

(A)

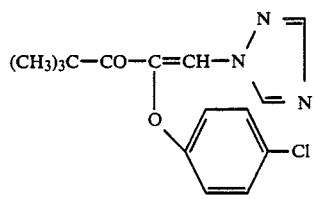

(B)

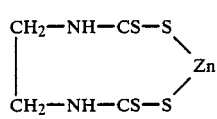

(C)

EXAMPLE A

Venturia test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following preparation examples: 1, 3, 6, 4, 19, 24 and 26.

EXAMPLE B

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae.* The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples: 8, 23, 24 and 25.

EXAMPLE C

Pyricularia test (rice)/systemic

Solvent: 12.5 parts by weight of acetone

Emulsifier: 0.3 parts by weight of alkylarly polyglycol ether

To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae.* Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 5, 10, 15, 23 and 24.

EXAMPLE D

*Cochliobolus sativus* test (barley)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Cochliobolus sativus.* The plants remain in an incubation cabinet for 48 hours at 20° C. and 100% relative atmospheric humidity.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds according to the following preparation examples: 1, 5, 7, 16, 18, 23, 24, 25, 26, 27, 28 and 29.

EXAMPLE E

*Drechslera graminea* test (barley)/seed treatment (syn. *Helminthosporium gramineum*)

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

The seed is embedded in sieved, moist standard soil and is exposed to a temperature of 4° C. in closed Petri dishes in a refrigerator for 10 days. Germination of the barley, and possibly also of the fungus spores, is thereby initiated. 2 batches of 50 grains of the pregerminated barley are subsequently sown 3 cm deep in standard soil and are cultivated in a greenhouse at a temperature of about 18° C., in seedboxes which are exposed to light for 15 hours daily.

About 3 weeks after sowing, the plants are evaluated for symptoms of stripe disease.

In this test, a clearly superior activity compared with the prior art is shown, for example, by the compounds according to the following preparation examples: 24 and 26.

EXAMPLE F

Test on scab mites

Screening test on Psoroptes ovis/contact test in vitro

Test subject: All the development stages of Psoroptes ovis removed as skin scrapings from artificially infected cattle 1 hour before the start of the test.

Test method: Transfer of 10–25 mites/concentration to 1 ml of the active compound concentratio to be tested. Subsequent transfer to and storage in a climatically controlled test room (28° C.+1° C., 80% relative humidity ±10%). Check on the action after 24 hours with a stereomicroscope, 12.5-fold magnification).

Criteria: The occurrence of the death of the treated mites is the action criterion (sign of death=absence of voluntary movements of the limbs following stimulation with a dissection needle).

Evaluation: 100% action=all the mites have been destroyed, >50% action=more than 50% of the mites have been destroyed, <50% action=less than 50% of the mites have been destroyed, no action=all the mites are alive.

In this test, for example, the compounds according to Preparation Examples 22 and 29 exhibit a very good action (100% destruction).

It will be understood that the specification and examples are illustrative but not limitative of the present invention and that other embodiments within the spirit and scope of the invention will suggest themselves to those skilled in the art.

What is claimed is:

1. An azolylvinyl ether of the formula 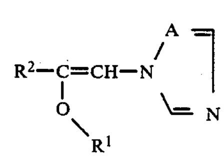 in which

A represents a nitrogen atom or the CH group, $R^1$ represents phenoxyalkyl with 1 or 2 carbon atoms in the alkyl part, or phenoxyalkoxyalkyl with 1 or 2 carbon atoms in each alkyl part and mono-, di- or tri-substituted by identical or different substituents on the phenyl part by substituents selected from fluorine, chlorine, straight-chain or branched alkyl with 1 to 4 carbon atoms, nitro, phenyl, phenylalkyl with 1 to 3 carbon atoms in the alkyl part, and cyclohexyl; or represents cylcohexylmethyl, or represents naphthoxyalkyl with 1 to 2 carbon atoms in the alkyl part;

$R^2$ represents straight-chain or branched alkyl with 1 to 6 carbon atoms, or represents fluorotert.-butyl, or the grouping $R^3$—C(CH$_3$)$_2$—, or represents cyclohexyl, or methylcyclohexyl; or furthermore also represents phenyl which is optionally mono, di- or tri-substituted by identical or different substituents as already mentioned for $R^1$ if $R^1$ represents optionally substituted phenoxyalkyl or optionally substituted phenoxyalkoxyalkyl and A represents a nitrogen atom; and $R^3$ represents phenoxyalkyl with 1 or 2 carbon atoms in the alkyl part, optionally mono-, di- or tri-substituted on the phenyl part by identical or different substituents as mentioned for $R^1$, or an addition product thereof with an acid or metal salt.

2. A compound according to claim 1, wherein such compound is 3,3-dimethyl-2-(4-chlorophenoxyethoxy)-1-(1,2,4-triazol-1-yl)-1-butene of the formula

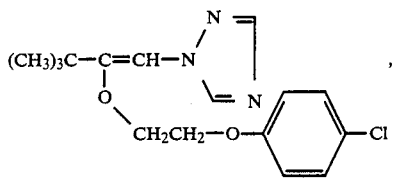

or an addition product thereof with an acid or metal salt.

3. A compound according to claim 1, wherein such compound is 3,3-dimethyl-2-(4-diphenyloxyethoxy)-1-(1,2,4-triazol-1-yl)-1-butene of the formula

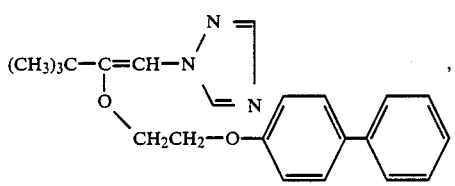

or an addition product thereof with an acid or metal salt.

4. A compound according to claim 1, wherein such compound is 3,3-dimethyl-2-(4-chlorophenoxyethoxy)-1-(imidazol-1-yl)-1-butene of the formula

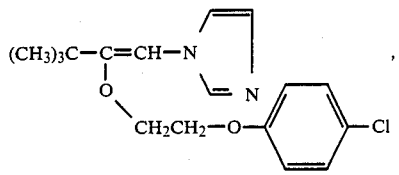

or an addition product thereof with an acid or metal salt.

5. A compound according to claim 1, wherein such compound is 3,3-dimethyl-2-(4-chloro-2-methyl-phenoxyethoxy)-1-(imidazol-1-yl)-1-butene of the formula

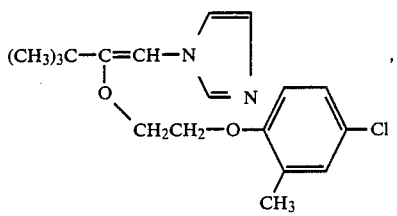

or an addition product thereof with an acid or metal salt.

6. A compound according to claim 1, wherein such compound is 3,3-dimethyl-2-($\beta$-naphthoxyethoxy)-1-(imidazol-1-yl)-1-butene of the formula

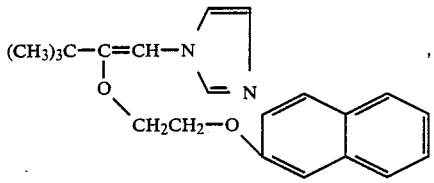

or an addition product thereof with an acid or metal salt.

7. A fungicidal or ectoparasiticidal composition comprising a fungicidally or ectoparasiticidally effective amount of a compound or addition product according to claim 1 in admixture with a diluent.

8. A method of combating fungi or ectoparasites which comprises applying to such fungi, ectoparasites or a habitat thereof a fungicidally or ectoparasiticidally effective amount of a compound or addition product according to claim 1.

9. The method according to claim 8, wherein such compound is
3,3-dimethyl-2-(4-chlorophenoxyethoxy)-1-(1,2,4-triazol-1-yl)-1-butene,
3,3-dimethyl-2-(4-diphenyloxyethoxy)-1-(1,2,4-triazol-1-yl)-1-butene,
3,3-dimethyl-2-(4-chlorophenoxyethoxy)-1-(imidazol-1-yl)-1-butene,
3,3-dimethyl-2-(4-chloro-2-methyl-phenoxyethoxy)-1-(imidazol-1-yl)-1-butene, or
3,3-dimethyl-2-($\beta$-naphthoxyethoxy)-1-(imidazol-1-yl)-1-butene,
or an addition product thereof with an acid or metal salt.

* * * * *

UNITED STATES PATENT AND TRADEMARK OFFICE
CERTIFICATE OF CORRECTION

PATENT NO. : 4,764,526
DATED : August 16, 1988
INVENTOR(S) : Klaus Böckmann, et al It is certified that error appears in the above-identified patent and that said Letters Patent is hereby corrected as shown below:

| | |
|---|---|
| Col. 1, line 25 | Correct --Schädlingsbekämpfungs-mittel-- |
| Col. 2 line 68 | After "tert" delete "," and substitute --.-- |
| Col. 3, line 49 and Col. 21, line 11 | After "fluoro" insert -- - -- |
| Col. 6, lines 10-11 | Delete "oranisms" and substitute --organisms-- |
| Col. 7, line 2 | Delete "pets" and substitute --pests-- |
| Col. 7, line 65 | Delete "Adhesive" and substitute --Adhesives-- |
| Col. 8, line 60 | Delete "1678 (1 mol)" and substitute --167g(1 mol)-- |
| Col. 10, line 4 | Correct --following-- |

Signed and Sealed this

Eleventh Day of April, 1989

Attest:

DONALD J. QUIGG

Attesting Officer  Commissioner of Patents and Trademarks